United States Patent
Rajappan et al.

(10) Patent No.: US 10,625,222 B1
(45) Date of Patent: Apr. 21, 2020

(54) PROCESS AND APPARATUS FOR CONTROLLING ANTI-FOAM INJECTION USING A DIFFERENTIAL PRESSURE TRANSMITTER

(71) Applicant: UOP LLC, Des Plaines, IL (US)

(72) Inventors: Rajesh Rajappan, Buffalo Grove, IL (US); Ryan Miller, Villa Park, IL (US)

(73) Assignee: UOP LLC, Des Plaines, IL (US)

( * ) Notice: Subject to any disclaimer, the term of this patent is extended or adjusted under 35 U.S.C. 154(b) by 91 days.

(21) Appl. No.: 16/146,795

(22) Filed: Sep. 28, 2018

(51) Int. Cl.
| | |
|---|---|
| *B01D 19/04* | (2006.01) |
| *B01F 5/04* | (2006.01) |
| *B05B 12/08* | (2006.01) |
| *C07C 7/00* | (2006.01) |
| *C07C 7/20* | (2006.01) |
| *B05B 12/12* | (2006.01) |

(52) U.S. Cl.
CPC ............ *B01F 5/0495* (2013.01); *B01D 19/04* (2013.01); *B05B 12/085* (2013.01); *B05B 12/12* (2013.01); *C07C 7/005* (2013.01); *C07C 7/20* (2013.01); *C10G 2400/30* (2013.01)

(58) Field of Classification Search
None
See application file for complete search history.

(56) References Cited

U.S. PATENT DOCUMENTS

| | | | |
|---|---|---|---|
| 3,264,365 A * | 8/1966 | Luken | C07C 7/08 585/501 |
| 5,108,655 A | 4/1992 | Johns, Jr. et al. | |
| 2006/0047146 A1* | 3/2006 | Wonders | B01J 4/002 562/414 |
| 2010/0200224 A1* | 8/2010 | Toguem Nguete | E21B 43/121 166/250.15 |
| 2010/0242594 A1 | 9/2010 | Onishi et al. | |

FOREIGN PATENT DOCUMENTS

| | | |
|---|---|---|
| GB | 1012809 | 12/1965 |
| WO | 2013142356 A1 | 9/2013 |
| WO | 2017200841 A1 | 11/2017 |

OTHER PUBLICATIONS

International Search report from PCT/US2019/053330, dated Dec. 5, 2019.
Written Opinion from PCT/US2019/053330, dated Dec. 5, 2019.

* cited by examiner

*Primary Examiner* — Tam M Nguyen

(57) ABSTRACT

The present invention relates to a process for controlling the antifoam injection based on the pressure differential of the column. More specifically, the present invention relates to a process for controlling the antifoam injection based on the pressure differential of an aromatics extraction unit using an intelligent differential pressure transmitter. The controller communicates with the antifoam injection system so that the antifoam is injected to the unit only when it is required.

10 Claims, No Drawings

PROCESS AND APPARATUS FOR CONTROLLING ANTI-FOAM INJECTION USING A DIFFERENTIAL PRESSURE TRANSMITTER

FIELD

The present invention relates to a process and apparatus for controlling the antifoam injection based on the pressure differential of the column. More specifically, the present invention relates to a process for controlling the antifoam injection based on the pressure differential of an aromatics extraction unit using an intelligent differential pressure transmitter. The controller communicates with the antifoam injection system so that the antifoam is injected to the unit only when it is required.

BACKGROUND

This underlying process is used to recover high-purity aromatics from hydrocarbon mixtures, such as reformed petroleum naphtha (reformate), pyrolysis gasoline (pygas), or coke-oven light oil. It can also be used for benzene reduction in fuels. The aromatics recovery process takes its name from the solvent used: tetrahydrothiophene-1, 1-dioxide, or sulfolane, which is the most efficient solvent available for the recovery of aromatics.

Many aromatics extraction units experience foaming which requires anti-foam injections. However, anti-foam particulates may be found downstream on the trays, especially the silica in the anti-foam. This causes fouling issues in the unit. The silica in the anti-foam may also appear in the raffinate in an aromatics extraction unit which can cause issues for downstream hydrotreating reactors.

SUMMARY

The present disclosure describes an intelligent controller that communicates with the antifoam injection system so that the antifoam is injected to the unit only when it is required. The symptoms of foaming are similar to flooding, especially indicated by a slow rising pressure drop across the column. The incipient flooding detected by the transmitter will send a signal to the antifoam injection pump to start the pump at a predetermined rate. A signal will again alert the operator if the current antifoam injection is not enough, by looking at the changes in the trend. The operator can adjust the antifoam rate, for example from 1 wt ppm of stripper feed to 2 wt ppm of stripper feed, to a higher rate if required. When the foaming subsides the antifoam can be reduced and completely stopped.

In the foregoing, all temperatures are set forth in degrees Celsius and, all parts and percentages are by weight, unless otherwise indicated. Other objects, advantages and applications of the present invention will become apparent to those skilled in the art from the following detailed description. Additional objects, advantages and novel features of the examples will be set forth in part in the description which follows, and in part will become apparent to those skilled in the art upon examination of the following description or may be learned by production or operation of the examples. The objects and advantages of the concepts may be realized and attained by means of the methodologies, instrumentalities and combinations particularly pointed out in the appended claims.

DETAILED DESCRIPTION

The following detailed description is merely exemplary in nature and is not intended to limit the application and uses of the embodiment described. Furthermore, there is no intention to be bound by any theory presented in the preceding background or the following detailed description.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "stream" can include various hydrocarbon molecules and other substances. Moreover, the term "stream comprising Cx hydrocarbons" can include a stream comprising hydrocarbon with "x" number of carbon atoms, suitably a stream with a majority of hydrocarbons with "x" number of carbon atoms and preferably a stream with at least 75 wt % hydrocarbon molecules, respectively, with "x" number of carbon atoms. Moreover, the term "stream comprising Cx+ hydrocarbons" can include a stream comprising a majority of hydrocarbon molecules, with more than or equal to "x" carbon atoms and suitably less than 10 wt % and preferably less than 1 wt % hydrocarbon molecules, with x−1 carbon atoms. Lastly, the term "Cx− stream" can include a stream comprising a majority of hydrocarbon molecules with less than or equal to "x" carbon atoms and suitably less than 10 wt % and preferably less than 1 wt % hydrocarbon molecules, with x+1 carbon atoms.

The term "column" means a distillation column or columns for separating one or more components of different volatilities. Unless otherwise indicated, each column includes a condenser on an overhead of the column to condense the overhead vapor and reflux a portion of an overhead stream back to the top of the column. Also included is a reboiler at a bottom of the column to vaporize and send a portion of a bottom stream back to the bottom of the column to supply fractionation energy. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

As used herein, the term "overhead stream" can mean a stream withdrawn at or near a top of a vessel, such as a column.

As used herein, the term "bottoms stream" can mean a stream withdrawn at or near a bottom of a vessel, such as a column.

The various embodiments described herein relate to a process for detecting levels of anti-foam in an aromatics extraction unit using an intelligent differential pressure transmitter. The symptoms of foaming are similar to flooding, especially indicated by a slow rising pressure drop across the column. The incipient flooding detected by the transmitter will send a signal to the antifoam injection pump to start the pump at a predetermined rate. A signal will again alert the operator if the current antifoam injection is not enough, by looking at the changes in the trend. The operator can adjust the antifoam rate, for example from 1 wt ppm of stripper feed to 2 wt ppm of stripper feed, to a higher rate if required. When the foaming subsides the antifoam can be reduced and completely stopped.

The benefits to the process for detecting levels of anti-foam in an aromatics extraction unit include low cost of installation on an existing unit, reducing the adverse effects of the sustained antifoam injection and unnecessarily wasting antifoam, and improving the reliability of the unit thus reducing downtown.

Here, the process for controlling anti-foam injection in an aromatics extraction unit includes measuring the pressure at various points. The pressure may be measured using pressure sensors. For example, measuring the pressure of the section between a lean solvent injection point and a feed point, measuring the pressure of the section between an overhead and the lean solvent point, and determining the pressure difference of the section between lean solvent injection point and the feed point and the section between the overhead and the lean solvent point. Further, measuring the pressure of the section between lean solvent injection point and the feed point, measuring the pressure of the section between the feed point and the bottom of the column, and determining the pressure difference of the section between lean solvent injection point and the feed point and the section between the feed point and the bottom of the column. Then lastly measuring the pressure of the section between lean solvent injection point and the feed point, measuring the pressure of the section between the lean solvent injection point and the top tray of the column, and determining the pressure difference of the section between lean solvent injection point and the feed point and the section between the lean solvent injection point and the top tray of the column. Using the pressure differential information, a decision may be made to adjust the flow rate of the anti-foam injection.

There may be a signal will again alert the operator if the current antifoam injection is not enough, by looking at the changes in the trend. The operator can adjust the antifoam rate to a higher rate if required. For example, the operator may adjust the anti-foam rate from about 1 wt ppm of stripper feed to about 2 wt ppm of stripper feed. Then when the foaming subsides the anti-foam can be reduced and completely stopped. In some examples the antifoam comprises poly dimethyl siloxanes. The anti-foam may need to be mixed before injection.

While the invention has been described with what are presently considered the preferred embodiments, it is to be understood that the invention is not limited to the disclosed embodiments, but it is intended to cover various modifications and equivalent arrangements included within the scope of the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for controlling anti-foam injection in an aromatics extraction unit, comprising measuring the pressure of the section between a lean solvent injection point and a feed point; measuring the pressure of the section between an overhead and the lean solvent point; determining the pressure difference of the section between lean solvent injection point and the feed point and the section between the overhead and the lean solvent point; measuring the pressure of the section between lean solvent injection point and the feed point; measuring the pressure of the section between the feed point and the bottom of the column; determining the pressure difference of the section between lean solvent injection point and the feed point and the section between the feed point and the bottom of the column; measuring the pressure of the section between lean solvent injection point and the feed point; measuring the pressure of the section between the lean solvent injection point and the top tray of the column; determining the pressure difference of the section between lean solvent injection point and the feed point and the section between the lean solvent injection point and the top tray of the column; and adjusting the flow rate of the anti-foam injection. An embodiment of the invention is one, any or all of prior embodiments in this paragraph up through the first embodiment in this paragraph, wherein a pressure differential of determines foaming. An embodiment of the invention is one, any or all of prior embodiments in this paragraph up through the first embodiment in this paragraph, wherein detecting the pressure differential sends a signal to the antifoam injection pump to start the pump at a predetermined rate. An embodiment of the invention is one, any or all of prior embodiments in this paragraph up through the first embodiment in this paragraph, wherein a signal will again alert the operator if the current antifoam injection is not enough, by looking at the changes in the trend. An embodiment of the invention is one, any or all of prior embodiments in this paragraph up through the first embodiment in this paragraph, wherein an operator can adjust the antifoam rate to a higher rate if required. An embodiment of the invention is one, any or all of prior embodiments in this paragraph up through the first embodiment in this paragraph, wherein the operator may adjust the anti-foam rate from about 1 wt ppm of stripper feed to about 2 wt ppm of stripper feed. An embodiment of the invention is one, any or all of prior embodiments in this paragraph up through the first embodiment in this paragraph, wherein when the foaming subsides the anti-foam can be reduced and completely stopped. An embodiment of the invention is one, any or all of prior embodiments in this paragraph up through the first embodiment in this paragraph, wherein the antifoam comprises poly dimethyl siloxanes. An embodiment of the invention is one, any or all of prior embodiments in this paragraph up through the first embodiment in this paragraph, wherein 105 wt ppm anti-foam is injected when necessary. An embodiment of the invention is one, any or all of prior embodiments in this paragraph up through the first embodiment in this paragraph, wherein the anti-foam is mixed before injection. An anti-foam injection system, comprising a first measuring device in fluid communication with a first pressure source; a second measuring device in fluid communication with a second pressure source; an anti-foam dosing unit in fluid communication with an aromatics extraction unit; and a controller. An embodiment of the invention is one, any or all of prior embodiments in this paragraph up through the first embodiment in this paragraph, wherein the first measuring device comprises a pressure sensor. An embodiment of the invention is one, any or all of prior embodiments in this paragraph up through the first embodiment in this paragraph, wherein the second measuring device comprises a pressure sensor. An embodiment of the invention is one, any or all of prior embodiments in this paragraph up through the first embodiment in this paragraph, wherein the controller measures the pressure differential. An embodiment of the invention is one, any or all of prior embodiments in this paragraph up through the first embodiment in this paragraph, wherein the controller sends a signal to the antifoam injection pump to start the pump at a predetermined rate. An embodiment of the invention is one, any or all of prior embodiments in this paragraph up through the first embodiment in this paragraph, wherein a signal will again alert the operator if the current antifoam injection is not enough, by looking at the changes in the trend. An embodiment of the invention is one, any or all of prior embodiments in this paragraph up through the first embodiment in this paragraph, wherein an operator can adjust the antifoam rate to a higher rate if required. An embodiment of the invention is one, any or all of prior embodiments in this paragraph up through the first embodiment in this paragraph, wherein the operator may adjust the anti-foam rate from about 1 wt ppm of stripper feed to about 2 wt ppm of stripper feed. An embodiment of the invention is one, any or all of prior embodiments in this paragraph up through the first embodiment in this paragraph, wherein when the foaming subsides the anti-foam can be reduced and completely stopped. An embodiment of the invention is one, any or all of prior embodiments in this paragraph up through the first embodiment in this paragraph, wherein the antifoam comprises poly dimethyl siloxanes.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for controlling anti-foam injection in an aromatics extraction unit, comprising:
    measuring the pressure of the section between a lean solvent injection point and a feed point;
    measuring the pressure of the section between an overhead and the lean solvent point;
    determining the pressure difference of the section between lean solvent injection point and the feed point and the section between the overhead and the lean solvent point;
    measuring the pressure of the section between lean solvent injection point and the feed point;
    measuring the pressure of the section between the feed point and the bottom of the column;
    determining the pressure difference of the section between lean solvent injection point and the feed point and the section between the feed point and the bottom of the column;
    measuring the pressure of the section between lean solvent injection point and the feed point;
    measuring the pressure of the section between the lean solvent injection point and the top tray of the column;
    determining the pressure difference of the section between lean solvent injection point and the feed point and the section between the lean solvent injection point and the top tray of the column; and
    adjusting the flow rate of the anti-foam injection.

2. The process of claim 1, wherein a pressure differential of determines foaming.

3. The process of claim 1, wherein detecting the pressure differential sends a signal to the antifoam injection pump to start the pump at a predetermined rate.

4. The process of claim 1, wherein a signal will again alert the operator if the current antifoam injection is not enough, by looking at the changes in the trend.

5. The process of claim 1, wherein an operator can adjust the antifoam rate to a higher rate if required.

6. The process of claim 1, wherein the operator may adjust the anti-foam rate from about 1 wt ppm of stripper feed to about 2 wt ppm of stripper feed.

7. The process of claim 1, wherein when the foaming subsides the anti-foam can be reduced and completely stopped.

8. The process of claim 1, wherein the antifoam comprises poly dimethyl siloxanes.

9. The process of claim 1, wherein 105 wt ppm anti-foam is injected when necessary.

10. The process of claim 1, wherein the anti-foam is mixed before injection.

* * * * *